US009612306B2

(12) United States Patent
Lin et al.

(10) Patent No.: US 9,612,306 B2
(45) Date of Patent: Apr. 4, 2017

(54) METHOD FOR ASSESSING REPETITIVE HEAD INJURIES WITH TWO-DIMENSIONAL MAGNETIC RESONANCE SPECTROSCOPY

(75) Inventors: Alexander Lin, Newton, MA (US); Carolyn Mountford, East Ryde (AU); Saadallah Ramadan, Bexley (AU); Robert Stern, Boston, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 982 days.

(21) Appl. No.: 13/988,813

(22) PCT Filed: Nov. 28, 2011

(86) PCT No.: PCT/US2011/062211
§ 371 (c)(1),
(2), (4) Date: Sep. 16, 2013

(87) PCT Pub. No.: WO2012/071584
PCT Pub. Date: May 31, 2012

(65) Prior Publication Data
US 2014/0002075 A1    Jan. 2, 2014

Related U.S. Application Data

(60) Provisional application No. 61/417,348, filed on Nov. 26, 2010.

(51) Int. Cl.
*G01R 33/483*    (2006.01)
*A61B 5/055*    (2006.01)
(Continued)

(52) U.S. Cl.
CPC ........... *G01R 33/483* (2013.01); *A61B 5/055* (2013.01); *A61B 5/4064* (2013.01);
(Continued)

(58) Field of Classification Search
CPC .... G01R 33/483; G01R 33/485; A61B 5/055; A61B 5/4064; A61B 2503/00; A61B 2503/04; A61B 2503/10
See application file for complete search history.

(56) References Cited

U.S. PATENT DOCUMENTS 5,318,031 A    6/1994   Mountford et al.
6,475,998 B1 *  11/2002  Soreq ................. A61K 31/137
                                                     435/325

(Continued)

OTHER PUBLICATIONS

International Search Report and Written Opinion under date of mailing of Jun. 21, 2012 in connection with PCT/US2011/062211.

*Primary Examiner* — Dixomara Vargas
(74) *Attorney, Agent, or Firm* — Quarles & Brady LLP

(57) ABSTRACT

A method for producing a biomarker indicative of a repetitive head injury in a subject using a magnetic resonance imaging (MRI) system is provided. Two-dimensional spectroscopic data is acquired from a subject using an MRI system. From the two-dimensional spectroscopic data, a two-dimensional spectrum is produced. The two-dimensional spectrum contains spectral information indicated by a first spectral dimension and a second spectral dimension. Such a two-dimensional spectrum may include diagonal peaks and off-diagonal, or cross-peaks. In such an instance, each cross peak may indicate, for example, scalar coupling between the two protons it connects on the diagonal. However, depending on the type of method used, different types of coupling may also be present. Using the two-dimensional spectrum, a biomarker indicative of repetitive head injury in the subject is identified, and may be used to produce a report indicating a status or regression of a neurological dysfunction.

15 Claims, 2 Drawing Sheets

(51) Int. Cl.
*A61B 5/00* (2006.01)
*G01R 33/485* (2006.01)

(52) U.S. Cl.
CPC ....... *A61B 2503/00* (2013.01); *A61B 2503/04* (2013.01); *A61B 2503/10* (2013.01); *G01R 33/485* (2013.01)

(56) References Cited

U.S. PATENT DOCUMENTS

| | | | |
|---|---|---|---|
| 6,887,199 B2 * | 5/2005 | Bridger | A61B 5/02438 128/920 |
| 7,112,319 B2 * | 9/2006 | Broderick | A61B 5/14542 424/1.11 |
| 7,396,654 B2 * | 7/2008 | Hayes | C12Q 1/6883 435/4 |
| 7,611,858 B1 * | 11/2009 | Svetlov | C07K 16/28 435/7.95 |
| 8,298,835 B2 * | 10/2012 | Wang | C12Q 1/37 422/430 |
| 8,492,107 B2 * | 7/2013 | Wang | C07K 16/18 435/4 |
| 9,145,372 B2 * | 9/2015 | Lowe, III | A61K 31/50 |
| 9,192,333 B1 * | 11/2015 | Hayes | A61B 5/7264 |
| 9,482,675 B1 * | 11/2016 | Lovell | G01N 33/6872 |
| 9,489,731 B2 * | 11/2016 | Schneider | A61B 5/055 |
| 2002/0142367 A1 | 10/2002 | Ke et al. | |
| 2005/0022168 A1 * | 1/2005 | Zhu | G06F 19/24 717/124 |
| 2009/0247860 A1 * | 10/2009 | Djuric | G01N 24/08 600/420 |
| 2010/0016706 A1 | 1/2010 | Wohlgemuth | |

* cited by examiner

METHOD FOR ASSESSING REPETITIVE HEAD INJURIES WITH TWO-DIMENSIONAL MAGNETIC RESONANCE SPECTROSCOPY

CROSS-REFERENCE TO RELATED APPLICATIONS

This application represents the national stage entry of PCT International Application No. PCT/US2011/062211 filed on Nov. 28, 2011, and claims the benefit of U.S. Provisional Patent Application Ser. No. 61/417,348, filed on Nov. 26, 2010, and entitled "Method for Assessing Repetitive Head Injuries with Two-Dimensional Magnetic Resonance Spectroscopy." The disclosure of each of these applications is hereby incorporated by reference as if set forth in their entirety herein.

STATEMENT REGARDING FEDERALLY SPONSORED RESEARCH

This invention was made with Government support under Grant Number TR001102 awarded by the National Institutes of Health. The Government has certain rights in this invention.

BACKGROUND OF THE INVENTION

The field of the invention is systems and methods for magnetic resonance imaging ("MRI") and magnetic resonance spectroscopy ("MRS"). More particularly, the invention relates to systems and methods for assessing the effects of repetitive head injuries with MRS and magnetic resonance spectroscopic imaging ("MRSI").

Recent studies have demonstrated that changes in cerebral metabolites and other biochemicals after severe traumatic brain injury may correlate strongly with clinical grade and patient outcome. Most of these studies showed the following changes in both gray matter and white matter regions in patients with severe traumatic brain injury when compared to age-matched controls: a persistent reduction of N-acetyl aspartate ("NAA"), presence of lipid and lactate, and elevated concentrations of cerebral osmolytes, including choline and myo-inositol. For example, in a previous study by B. D. Ross, et al., titled "1H MRS in Acute Traumatic Brain Injury," *J. Magn. Reson. Imaging*, 1998; 8(4):829-840, it was shown that there are changes in cerebral metabolites after acute traumatic brain injury, and a strong correlation with clinical grade and patient outcome. This study showed that patients with traumatic brain injury, when compared to age-matched controls, exhibited a persistent reduction of NAA, a putative neuronal marker that indicates neuronal and axonal injury; presence of lipid and lactate, which are MRS markers of hypoxia; and elevated concentrations of cerebral osmolytes, including choline and myo-inositol, in both gray matter and white matter regions of the brain. This study was, however, limited to employing one-dimensional MRS techniques, which are incapable of measuring subtler changes in cerebral metabolites.

Sports-related brain injuries are milder, and potentially different types of head injuries altogether than severe, or even mild, traumatic brain injuries, making it more difficult to identify subtle changes in biochemical concentrations following such repetitive head injuries. Recent studies have shown that one of the long term effects of repetitive head injury is the neurodegenerative disease referred to as chronic traumatic encephalopathy ("CTE"). CTE is characterized, post mortem, by abnormal tau accumulation in the brain. However, there is currently no known technique for identifying early hallmarks of CTE and whether a patient subjected to repetitive head injuries is at risk for developing CTE.

In light of the foregoing, it would therefore be desirable to provide a method for non-invasively testing, in vivo, patients with repetitive head injury, such as athletes and soldiers, during the lifetime of the patient for diseases related to the repetitive head injury.

SUMMARY OF THE INVENTION

The present invention overcomes the aforementioned drawbacks by providing a system and method for magnetic resonance imaging ("MRI") and magnetic resonance spectroscopy ("MRS") that is sensitive to subtle biochemical changes associated with and indicative of repetitive head injuries.

It is an aspect of the invention to provide a method for assessing an effect of repetitive head injury in a subject using an MRI system. The method includes acquiring two-dimensional spectroscopic data from a subject using the MRI system, and producing therefrom a two-dimensional magnetic resonance ("MR") spectrum that contains spectral information indicated by a first spectral dimension and a second spectral dimension. A biomarker, or series of biomarkers, that includes information pertaining to biochemical changes in the subject is identified using the produced two-dimensional spectrum, and a stored biomarker, or series of stored biomarkers, representative of a known neurological state is provided for comparison against the identified biomarker or series of biomarkers. A report indicating the likelihood of similarity between the identified and stored biomarkers is then produced.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
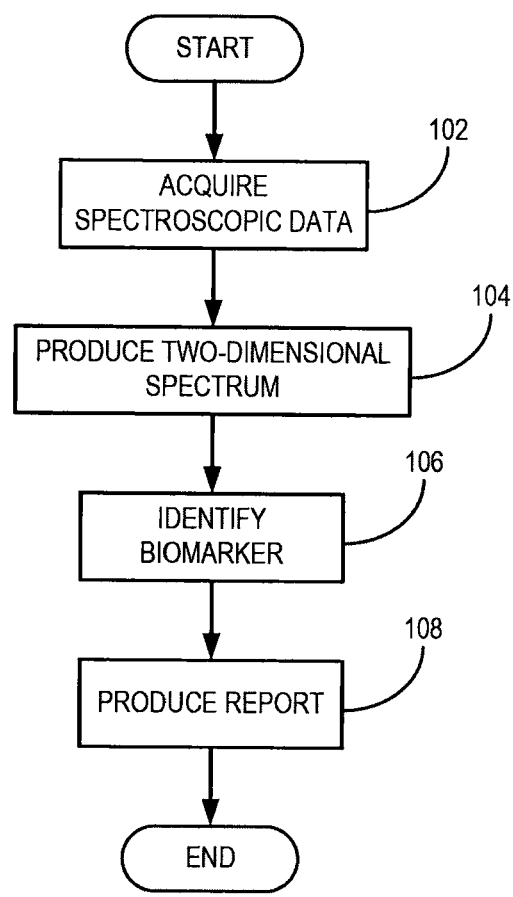
FIG. 1 is a flowchart setting for the steps of an example of a method for generating a biomarker indicative of traumatic brain injury using two-dimensional magnetic resonance spectroscopy.

The present invention provides a method for assessing repetitive head injuries by analyzing subtle changes in the concentration of cerebral metabolites, lipids, and other macromolecules, which may collectively be referred to as "biochemicals," using two-dimensional magnetic resonance spectroscopy ("MRS"). For example, the method provides a tool for the clinical assessment of an athlete or soldier following a head injury that may be one in a series of repetitive head injury events. The method of the present invention also provides a useful tool for determining whether a given head injury resulted in biochemical and structural degradations indicative of a longer term neurodegenerative disease, such as chronic traumatic encephalopathy ("CTE"). The method is also useful for assessing and monitoring biochemical and structural degradation and recovery, thereby providing a tool for assessing when a subject's brain has recovered from a prior head injury to a satisfactory clinical state. Another example of the clinical applicability of the present invention is in the field of pediatrics, where biochemical changes following sports-related concussions may be measured and used to identify the consequences of such injuries in children. Additionally, the methods of the present invention may also be useful for assessing shaken baby syndrome and for assessing the effects of a blast injury. Importantly, the present invention provides an objective measure of the effects of repetitive head injury on a patient and an objective indication as to whether the repetitive head injuries increase the risk of that patient developing a neurodegenerative disease. In this manner, the present invention provides a benefit to otherwise subjective determinations of the impact that repetitive head injury has on a patient and their subsequent healing process or continued deterioration and, thus, their clinical outcome.

Because repetitive head injuries are less severe than other brain traumas, including even mild traumatic brain injury, the biochemical changes produced by these repetitive injuries are subtler and more difficult to measure with conventional one-dimensional MRS techniques. To address this technical challenge, a two-dimensional MRS technique, such as two-dimensional correlated spectroscopy ("2D-COSY"), is employed, which is capable of not only detecting smaller changes in biochemical concentrations, but of identifying individual changes in molecules that are strongly coupled and, therefore, difficult to measure in vivo with one-dimensional MRS. It should be appreciated by those ordinarily skilled in the art that two-dimensional MRS techniques other than 2D-COSY may be implemented when practicing methods of the present invention.

By using two-dimensional MRS, the more subtle biochemical changes brought about by a repetitive head injury event can be reliably detected, measured, and analyzed. More particularly, two-dimensional MRS allows for identifying those specific biochemicals that change in response to a repetitive head injury event, and for determining how those biochemicals change with respect to each other. Thus, by using two-dimensional MRS, two-dimensional spectra can be generated, and in such spectra a pattern of biochemical changes in the brain following a repetitive head injury event can be reliably identified. Such patterns of biochemical changes in the two-dimensional spectra may be referred to as biomarkers indicative of repetitive head injury. It is contemplated that to increase the efficiency of the provided method for assessing the effects of repetitive head injury, pattern recognition classifiers can be employed to analyze differences in the identified biomarkers. Such classifiers may be based on data acquired across different patient groups and can be used for automated diagnosis on a clinical scanner. Examples of classifiers may include those classifiers indicating a normal, healthy brain, a mildly injured brain having a low risk for long term neurodegeneration, and a more severely injured brain having a moderate to high risk for long term neurodegeneration. The methods of the present invention can also report on those brains which are able to heal themselves and those which will continue to deteriorate.

Exposure to additional head injuries may lead to an increased likelihood in the development of CTE later in life. To date, research into CTE has been limited to the pathological analysis of the central nervous system post mortem via autopsy. As a result, little is known about the ways in which CTE clinically manifests and how it relates to prior repetitive head injuries. Thus, before CTE can be prevented, treated, diagnosed, or fully understood, more specific information about its clinical presentation and the development of appropriate biomarkers is required. Methods of the present invention provide tools for assessing and identifying the early hallmarks of CTE, such that a clinical diagnosis of CTE may be reached while a patient is still living. By providing tools for identifying the early hallmarks of CTE, clinicians will be able to develop methods for providing therapy to patients, treating patient, and monitoring changes in patients and their clinical outcome. Based on hypothesized mechanisms of CTE pathogenesis, it is contemplated that specific biomarkers may be identified and used to identify early indications of CTE in vivo. For instance, two-dimensional MRS is capable of detecting changes that include, but are not limited to, in glutamate, glutamine, aspartate, histamine, N-acetyl aspartate ("NAA"), gamma-aminobutyric acid ("GABA"), and myo-inositol. Patterns of changes in these subtle molecular species can serve as biomarkers of brain damage caused by repetitive head injury, and of neurodegeneration, or of recovery.

MRS is a non-invasive method for the measurement of brain biochemistry that provides a "virtual biopsy," whereby each resonance in the spectrum represents a chemical or brain metabolite whose height is correlated with its relative concentration to others present in the spectrum. The earlier stages of biochemical brain dysfunction are characterized by increased metabolic activity, including increased neuronal activity that includes glutamatergic dysfunction. As noted, current one-dimensional MRS methods can only measure glutamine and glutamate in combination because of the strong coupling and overlap of these chemicals with other metabolites; however, using appropriate two-dimensional MRS techniques, these strong couplings and overlaps may be teased apart, thereby opening the possibility that these measures may be used for clinically viable, separate measurements of glutamine and glutamate. These molecules can be separated by spectral editing methods, but such methods allow for only one of the many molecules to be measured at a time. Moreover, relative ratios cannot be determined using such methods.

MRS obtains chemical signals from metabolites in a region-of-interest ("ROI") or voxel location. In one-dimensional MRS, a spectrum of peaks is generated, in which each peak is indicative of resonance at a specific frequency that reflects the relative concentration of each metabolite in the ROI or at the voxel location. A number of metabolites relevant to brain trauma can be measured with one-dimensional MRS, including lipids, lactate, NAA, combined glutamate and glutamine, choline, myo-inositol, aspartate, histidine, GABA, and creatine. Although lipids are present throughout the brain in the form of cellular membranes, they are not typically "MR visible" unless liberated by a severe pathological process, including brain trauma. Lactate is detected in oxygen starved brain tissue. The presence of lactate in spectra indicates impairment of perfusion and is indicative of poor clinical outcome. NAA is an amino-acid derivative synthesized in neurons and transported down axons. Generally, NAA may be a marker of viable neurons, axons, and dendrites. Usually, brain injury is associated with decreased levels of NAA. Glutamate is the primary excitatory neurotransmitter in the brain and is tightly coupled to glutamine, which is found in the astrocytes. Aspartate increases in parallel with glutamate. Studies have shown that the combined glutamate and glutamine resonance is predictive of outcome in severe traumatic brain injury. Choline is a cellular membrane marker used to measure the changes in brain tissue. Because the majority of choline-containing brain constituents are not normally soluble, pathological alterations in membrane turnover result in an increase in MRS visible choline. Myo-inositol is an astrocyte marker and osmolyte. It is also involved in the metabolism of phosphatidyl inositol, a membrane phospholipid, and similar to choline is expected to increase due to membrane damage. Increased myo-inositol and choline are indicative of diffuse axonal injury. Creatine is used as an internal reference for the measurement of other metabolite peaks. For example, most MRS reports examine ratios of NAA-to-creatine, choline-to-creatine, and myo-inositol-to-creatine.

In one-dimensional MRS, many of the resonances are composite or overlap, and when spectral editing methods are employed, only one species can be examined at a time. Two-dimensional MRS, such as the 2D-COSY method, can be employed to separate these composite or overlapping resonance peaks in a second frequency dimension. While it is possible to use spectral editing techniques to identify metabolites that overlap in one-dimensional MRS, the advantage of the two-dimensional methods, such as 2D-COSY, is that the second frequency reveals all chemical species within a single scan. In general, a 2D-COSY data set is a series of one-dimensional spectra, each with increments in delay time inserted before the terminal readout radio frequency ("RF") pulse. The series of one-dimensional free induction decays ("FID") are Fourier transformed along the first dimension, followed by another Fourier transform in the second dimension. This generates a two-dimensional COSY spectrum that contains diagonal and off-diagonal (cross) peaks. Each cross peak indicates scalar coupling between the two protons it connects on the diagonal. Using this method, glutamate, glutamine, and numerous other metabolites, including those discussed above, can be accurately separated and identified. One benefit with two-dimensional MRS techniques, such as 2D-COSY, is that changes in diagonal peaks and cross-peaks may be compared relative to each other. In this manner, it is possible to detect changes in concentrations of specific biochemicals.

The following biochemicals have been found to be involved in repetitive head injury, and can be measured with two-dimensional MRS techniques, such as 2D-COSY: glutamate, aspartate, threonine, lipids and macromolecules, gamma-aminobutyric acid ("GABA"), and histidine. Glutamate is a major excitatory neurotransmitter. Brain dialysate studies show increased glutamate to be predictive of poor outcome when elevated in types of head injury other than those commonly reported as repetitive head injuries, including severe traumatic brain injury. Aspartate is an excitatory amino acid released into extracellular space after traumatic brain injury, and increased with glutamate. Threonine is a structural amino acid that appears to be released when tissue is damaged. Acute brain injury initiates a metabolic cascade that includes activation of phospholipase, resulting in the accumulation of lipid and macromolecules. GABA and histidine are inhibitory neurotransmitters. GABA is initially increased in the brain after head injury and is thought to play a neuroprotective role. Histidine has been shown to be excreted for an extended period of time after head injury.

Contrary to the effects of severe and mild traumatic brain injury, which result in a decrease in NAA concentration levels, a milder repetitive head injury event has been found to have a more subtle increase in the concentration of NAA. Thus, one component of a biomarker indicative of a repetitive head injury event may be a slight increase in NAA concentration levels. More particularly, by monitoring subtle changes in NAA relative to other molecules, it is possible to identify the severity of a patient's current injury, as well as the severity of their long term prognosis. For example, it is possible to identify whether the repetitive head injury event has left the patient mostly healthy, or whether the event has increased the risk that the patient will experience neuronal damage or develop CTE. In addition to NAA, a repetitive head injury event has also been found to more subtly effectuate changes in the other aforementioned biochemicals.

As noted above, a two-dimensional MRS technique, such as 2D-COSY, is employed to acquire two-dimensional spectroscopic data from voxel locations, or from an ROI. In some instances, two-dimensional spectroscopic data may be acquired from voxels covering the whole brain. By way of example, 2D-COSY may be implemented using a repetition time of 1.5 s; a weak water suppression using WET; a spectral width of 2000 Hz; increments of 0.8 ms in sixty-four $t_1$ increments giving an indirect spectral width of around 12.50 Hz; eight averages per increment; and 1024 data points. Scan time for such an acquisition is on the order of eleven minutes. Raw 2D spectroscopic data may be concatenated into a two-dimensional numerical array for further processing. For example, a Felix-2007 package (Accelrys; San Diego, Calif.) may be used for spectral processing and analysis. Zero-padding or linear prediction may be implemented to double the original data size, followed by apodization with skewed sine-squared window functions, in both dimensions, may be applied prior to magnitude two-dimensional Fourier transform (2DFT). The in vivo 2D spectra may then be referenced to the prominent singlet diagonal peak of creatine ($f_2=f_1=3.02$ ppm). Cross-peak volumes may be measured as described by C. L. Lean, et al., in "Cell-Surface Fucosylation and Magnetic Resonance Spectroscopy Characterization of Human Malignant Colorectal Cells," *Biochemistry*, 1992; 31(45):11095-11105. The 2D spectroscopic data, which can unambiguously identify up to thirty-five different chemicals in the brain including glutamine, glutamate, phosphatidylcholine, glycerophosphatidylcholine, GABA, and individual amino acids, may then be correlated to traumatic brain injury metrics, such as CTE metrics, in order to identify biomarkers for traumatic brain injury or CTE.

In addition to 2D-COSY, other two-dimensional MRS methods may be implemented. For example, the localized COSY ("L-COSY") method, which unambiguously assigns chemical information by separating those resonances, may be used. With L-COSY each cross peak, depicting scalar coupling between protons on the diagonal, can be measured with statistical significance, thereby allowing for the reliable comparison of the healthy brain versus disease. By way of example, the L-COSY method may include using three shaped and spatially selective RF pulses, which is the minimum number of RF pulses that can be used for localization. RF shapes can be sine, Shinnar-Le-Roux ("SLR"), or any slice-selective pulse with suitable spectral bandwidth. By way of example, the excitation pulses may be sine RF pulses and the refocusing RF pulses may be optimized Mao pulses, such as those described by J. Mao, et al., in "Experimental Study of Optimal Selective 180° Radiofrequency Pulses," *J. Magn. Reson.*, 1988; 79(1):1-10. In this configuration, the first two RF pulses generate a spin-echo, and then the third RF acts as a spatially selective and coherence transfer pulse. The acquired spectroscopic data may be combined to improve signal-to-noise ratio by using residual water signal and relative channel weighting as described, for example, by M. A. Brown in "Time-Domain Combination of MR Spectroscopy Data Acquired Using Phased-Array Coils," *Magn. Reson. Med.,* 2004; 52:1207-1213.

Referring now to FIG. 1, a flowchart setting forth the steps of an example of a method for producing a biomarker indicative of repetitive head injury using a magnetic resonance imaging system is illustrated. The method generally begins with the acquisition of spectroscopic data from the subject using the MRI system, as indicated at step 102. Such spectroscopic data has at least two spectral dimensions, such as two-dimensional spectroscopic data. By way of example, the spectroscopic data is acquired using a two-dimensional correlated spectroscopy ("COSY") technique, a two-dimensional localized COSY ("L-COSY") technique, or other two-dimensional MRS methods. After the spectroscopic data is acquired, it is processed to produce a two-dimensional spectrum that depicts spectral peak and cross-peak information, as indicated at step 104. From this two-dimensional spectrum a biomarker indicative of repetitive head injury is identified, as indicated at step 106. For example, a pattern of changes in biochemical concentrations may be identified in the two-dimensional spectrum. One such pattern of changes may be a slight increase in NAA accompanied with an increase in glutamate and an increase in aspartate. Such a biomarker provides an indication as to the severity of a repetitive head injury event, and to the likelihood that the repetitive head injury event is representative of a longer-term neurological disease, such as chronic traumatic encephalopathy ("CTE"). To produce a report as to the state of the repetitive head injury, the biomarker is compared with a stored biomarker, as indicated at step 108. This stored biomarker may include, for example, a pattern of biochemical concentration levels for a healthy individual or for an individual with a known neurological disease state. For example, the stored biomarker may be an average biomarker generated by averaging the patterns of biochemical changes for a group of individuals with similar clinical presentation following a repetitive head injury event. In this manner, template biomarkers may be generated for different degrees of injury, such as whether a repetitive head injury event indicates a risk for long term neurodegeneration, or whether a repetitive head injury event indicates a risk for long term neurodegeneration. By comparing the identified biomarker with such a template biomarker, it may be possible to identify early indications of a neurodegenerative disease, such as CTE. Additionally, by comparing the identified biomarker with a stored template biomarker, it may be possible to observe the brain recovering following an injury.

It is noted that the stored biomarkers may be compared with different criteria in order to develop a diagnostic paradigm. For example, the stored biomarkers may include information that is related to classifiers developed by comparing two-dimensional MR spectra with subjective neurological tests for a population of patients with similar neurological presentation or biochemical states. Additionally, the stored biomarkers may include information obtained by comparing two-dimensional MR spectra independent of subjective neurological tests. In this latter instance, it may be possible to identify biomarkers that define multiple different states of injury to the brain. The identified patient biomarkers may then be compared to one or more of these stored biomarkers to identify that different state of injury to the brain which most closely resembles the identified patient biomarkers.

It is noted that the stored biomarkers may be compared with different criteria in order to develop a diagnostic paradigm. For example the stored biomarkers may include information that is related to classifiers developed by comparing two-dimensional MR spectra with subjective neurological tests for a population of patients with similar neurological presentation. Additionally, the stored biomarkers may include information obtained by comparing two-dimensional MR spectra independent of subjective neurological tests. In this latter instance, it may be possible to identify biomarkers that define multiple different states of injury to the brain independent of conventional neurological tests. These may be obtained from biochemical states that have an established disease endpoint, or from prior knowledge of the extent of the head injury due to biochemical malfunction. The identified patient biomarkers may then be compared to one or more of these stored biomarkers to identify that different state of injury to the brain which most closely resembles the identified patient biomarkers.

Figure 2:
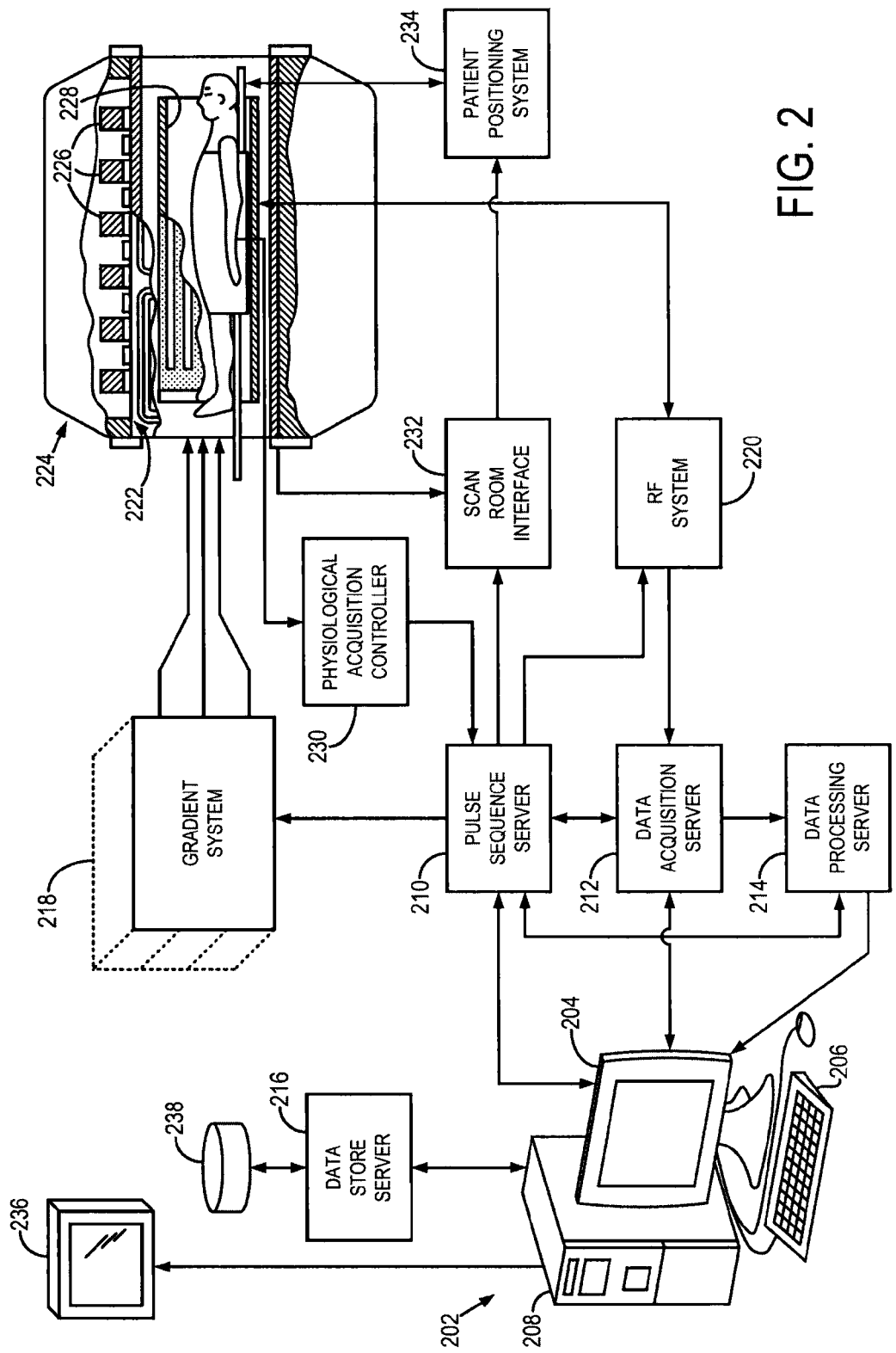
FIG. 2 is a block diagram of an example of a magnetic resonance imaging ("MRI") system.

Referring particularly now to FIG. 2, an exemplary magnetic resonance imaging ("MRI") system 200 is illustrated. The MRI system 200 includes a workstation 202 having a display 204 and a keyboard 206. The workstation 202 includes a processor 208, such as a commercially available programmable machine running a commercially available operating system. The workstation 202 provides the operator interface that enables scan prescriptions to be entered into the MRI system 200. The workstation 202 is coupled to four servers: a pulse sequence server 210; a data acquisition server 212; a data processing server 214; and a data store server 216. The workstation 202 and each server 210, 212, 214, and 216 are connected to communicate with each other.

The pulse sequence server 210 functions in response to instructions downloaded from the workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding MR signals. The gradient coil assembly 222 forms part of a magnet assembly 224 that includes a polarizing magnet 226 and a whole-body RF coil 228.

RF excitation waveforms are applied to the RF coil 228, or a separate local coil (not shown in FIG. 2), by the RF system 220 to perform the prescribed magnetic resonance pulse sequence. Responsive MR signals detected by the RF coil 228, or a separate local coil (not shown in FIG. 2), are received by the RF system 220, amplified, demodulated, filtered, and digitized under direction of commands produced by the pulse sequence server 210. The RF system 220 includes an RF transmitter for producing a wide variety of RF pulses used in MR pulse sequences. The RF transmitter is responsive to the scan prescription and direction from the pulse sequence server 210 to produce RF pulses of the desired frequency, phase, and pulse amplitude waveform. The generated RF pulses may be applied to the whole body RF coil 228 or to one or more local coils or coil arrays (not shown in FIG. 2).

The RF system 220 also includes one or more RF receiver channels. Each RF receiver channel includes an RF amplifier that amplifies the MR signal received by the coil 228 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad (1);$$

and the phase of the received MR signal may also be determined:

$$\varphi = \tan^{-1}\left(\frac{Q}{I}\right). \quad (2)$$

The pulse sequence server 210 also optionally receives patient data from a physiological acquisition controller 230. The controller 230 receives signals from a number of different sensors connected to the patient, such as electrocardiograph ("ECG") signals from electrodes, or respiratory signals from a bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized MR signal samples produced by the RF system 220 are received by the data acquisition server 212. The data acquisition server 212 operates in response to instructions downloaded from the workstation 202 to receive the real-time MR data and provide buffer storage, such that no data is lost by data overrun. In some scans, the data acquisition server 212 does little more than pass the acquired MR data to the data processor server 214. However, in scans that require information derived from acquired MR data to control the further performance of the scan, the data acquisition server 212 is programmed to produce such information and convey it to the pulse sequence server 210. For example, during prescans, MR data is acquired and used to calibrate the pulse sequence performed by the pulse sequence server 210. Also, navigator signals may be acquired during a scan and used to adjust the operating parameters of the RF system 220 or the gradient system 218, or to control the view order in which k-space is sampled.

The data processing server 214 receives MR data from the data acquisition server 212 and processes it in accordance with instructions downloaded from the workstation 202. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 214 are conveyed back to the workstation 202 where they are stored. Real-time images are stored in a data base memory cache (not shown in FIG. 2), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the workstation 202. The workstation 202 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for assessing an effect of repetitive head injury in a subject using a magnetic resonance imaging (MRI) system, the steps of the method comprising:
   a) acquiring two-dimensional magnetic resonance (MR) spectroscopic data from a subject using an MRI system;
   b) producing a two-dimensional MR spectrum from the two-dimensional MR spectroscopic data acquired in step a), the two-dimensional MR spectrum containing spectral information indicated by a first spectral dimension and a second spectral dimension;
   c) identifying a biomarker that includes information pertaining to a pattern of biochemical changes in the subject using the two-dimensional MR spectrum produced in step b);
   d) providing a stored biomarker associated with at least one of an extent of a brain injury and a neurological dysfunction for comparison against the biomarker identified in step c); and
   e) producing a report indicating a likelihood of similarity between the biomarker identified in step c) and the stored biomarker provided in step d).

2. The method as recited in claim 1 in which the stored biomarker is indicative of a healthy brain biochemical state.

3. The method as recited in claim 1 in which the stored biomarker is indicative of an early indication of a neurological dysfunction.

4. The method as recited in claim 3 in which the neurological dysfunction is indicative of chronic traumatic encephalopathy.

5. The method as recited in claim 1 in which step e) includes performing pattern recognition using the biomarker identified in step c) and the stored biomarker provided in step d).

6. The method as recited in claim 1 in which step c) includes assigning relative measures of biochemical concentrations to the biomarker.

7. The method as recited in claim 6 in which the biomarker identified in step c) indicates a change in relative measures of at least one of N-acetyl aspartate, glutamate, glutamine, histidine, lysine, threonine, choline, creatine, myo-inositol, taurine, citrate, fucose, aspartate, gamma aminobutyric acid (GABA), macromolecules, and lipids.

8. The method as recited in claim 7 in which the change in the relative measure of N-acetyl aspartate is an increase, the change in the relative measure of glutamate is an increase, and the change in the relative measure aspartate is an increase.

9. The method as recited in claim 1 in which step a) further includes acquiring one-dimensional MR spectroscopic data from the subject, step b) further includes producing a one-dimensional MR spectrum from the one-dimensional MR spectroscopic data acquired in step a), and step c) further includes identifying the biomarker using one-dimensional MR spectrum produced in step b).

10. The method as recited in claim 1 in which step c) includes identifying a plurality of biomarkers in the two-dimensional MR spectrum produced in step b).

11. The method as recited in claim 10 in which step d) includes providing a plurality of biomarkers of known neurological states for comparison against the biomarkers identified in step c).

12. The method as recited in claim 11 in which step e) includes producing a report indicating a likelihood of similarity between at least one of the plurality of biomarkers identified in step c) and at least one of the stored biomarkers provided in step d).

13. The method as recited in claim 1 in which step a) includes performing a two-dimensional correlated spectroscopy (2D-COSY) acquisition to acquire the two-dimensional MR spectroscopic data.

14. The method as recited in claim 1 in which the stored biomarker provided in step d) includes information related to classifiers developed by comparing two-dimensional MR spectra to subjective neurological tests.

15. The method as recited in claim 1 in which the stored biomarker provides in step d) includes information obtained by comparing two-dimensional MR spectra independent of subjective neurological tests.

* * * * *